United States Patent
Ziso et al.

(10) Patent No.: US 12,201,386 B2
(45) Date of Patent: Jan. 21, 2025

(54) ROBOTIC SYSTEM FOR MINIMALLY INVASIVE SURGERY

(71) Applicant: Technion Research & Development Foundation Limited, Haifa (IL)

(72) Inventors: Hadas Ziso, Kiryat-Tivon (IL); David Zarrouk, Jerusalem (IL); Moshe Shoham, Hoshaya (IL); Menashe Zaaroor, Tiberias (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 16/644,553

(22) PCT Filed: Sep. 6, 2018

(86) PCT No.: PCT/IL2018/051016
§ 371 (c)(1),
(2) Date: Mar. 5, 2020

(87) PCT Pub. No.: WO2019/049154
PCT Pub. Date: Mar. 14, 2019

(65) Prior Publication Data
US 2020/0261170 A1  Aug. 20, 2020

Related U.S. Application Data

(60) Provisional application No. 62/554,658, filed on Sep. 6, 2017.

(51) Int. Cl.
*A61B 34/30* (2016.01)
*A61B 17/00* (2006.01)
(Continued)

(52) U.S. Cl.
CPC .......... *A61B 34/30* (2016.02); *A61B 18/1477* (2013.01); *A61B 18/22* (2013.01);
(Continued)

(58) Field of Classification Search
CPC ..... A61B 34/30; A61B 18/1477; A61B 18/22; A61B 2034/302; A61B 34/32;
(Continued)

(56) References Cited

U.S. PATENT DOCUMENTS

2006/0085048 A1   4/2006  Cory et al.
2009/0177081 A1*  7/2009  Joskowicz ............. A61B 90/13
                                                              600/426
(Continued)

FOREIGN PATENT DOCUMENTS

CN      101120890       2/2008
CN      105636654       6/2016
(Continued)

OTHER PUBLICATIONS

Hadjipanayis, C. G., Widhalm, G., & Stummer, W. (2015). What is the Surgical Benefit of Utilizing 5-Aminolevulinic Acid for Fluorescence-Guided Surgery of Malignant Gliomas?. Neurosurgery, 77(5), 663-673. https://doi.org/10.1227/NEU.0000000000000929 (Year: 2015).*

(Continued)

*Primary Examiner* — Aaron F Roane
*Assistant Examiner* — Ranjani Mari Sundaresan

(57) ABSTRACT

Systems and methods for performing minimally invasive surgical procedures, especially for removal of tumors, and especially for brain tumors, using a robotically inserted therapeutic probe, which first detects tumorous tissue on a pre-planned path through the patient's tissue, before performing therapeutic procedures on the tissue, such as ablation. This pre-treatment detection procedure is thus able to avoid the destruction of healthy tissue. This also ensures that the therapeutic process indicated in a preoperative surgical plan is only performed on tumorous tissue, without sole reliance on preoperative image indications. This is important (Continued)

for neurosurgical operations performed on the brain, since preoperative images may not be accurate due to brain shift occurring during the procedure. Detection can be performed optically or ultrasonically, and treatment by laser or RF ablation. The probe insertion can be performed at 90° to the insertion axis of the device, thus minimizing passage through healthy tissue.

28 Claims, 4 Drawing Sheets

(51) Int. Cl.
| | | |
|---|---|---|
| A61B 18/00 | (2006.01) | |
| A61B 18/02 | (2006.01) | |
| A61B 18/14 | (2006.01) | |
| A61B 18/20 | (2006.01) | |
| A61B 18/22 | (2006.01) | |
| A61B 34/32 | (2016.01) | |
| A61B 90/00 | (2016.01) | |
| A61B 90/10 | (2016.01) | |

(52) U.S. Cl.
CPC .............. *A61B 2017/00057* (2013.01); *A61B 2018/00446* (2013.01); *A61B 2018/00577* (2013.01); *A61B 2018/00875* (2013.01); *A61B 2018/0293* (2013.01); *A61B 2018/2005* (2013.01); *A61B 2034/302* (2016.02); *A61B 34/32* (2016.02); *A61B 2090/103* (2016.02); *A61B 2090/3614* (2016.02); *A61B 2090/378* (2016.02)

(58) Field of Classification Search
CPC ...... A61B 2090/103; A61B 2090/3614; A61B 2090/378; A61B 2017/00057; A61B 2018/00446; A61B 2018/00577; A61B 2018/00875; A61B 2018/0293; A61B 2018/2005; A61B 2034/2059; A61B 2090/363; A61B 2090/306; A61B 2017/00026; A61B 2090/062; A61B 2034/301
See application file for complete search history.

(56) References Cited

U.S. PATENT DOCUMENTS

| | | |
|---|---|---|
| 2010/0179522 A1 | 7/2010 | Companion |
| 2011/0034912 A1* | 2/2011 | de Graff ................. A61B 5/01 606/21 |
| 2014/0025088 A1* | 1/2014 | Zarrouk ................. A61B 34/30 606/130 |
| 2016/0073909 A1 | 3/2016 | Zand et al. |
| 2016/0287308 A1 | 10/2016 | Grant |

FOREIGN PATENT DOCUMENTS

| | | |
|---|---|---|
| CN | 105748149 | 7/2016 |
| WO | WO 99/03397 | 1/1999 |
| WO | WO 2019/049154 | 3/2019 |

OTHER PUBLICATIONS

International Preliminary Report on Patentability Dated Mar. 19, 2020 From the International Bureau of WIPO Re. Application No. PCT/IL2018/051016. (9 Pages).
International Search Report and the Written Opinion Dated Dec. 26, 2018 From the International Searching Authority Re. Application No. PCT/IL2018/051016. (11 Pages).
Notification of Office Action Dated May 7, 2023 From the State Intellectual Property Office of the People's Republic of China Re. Application No. 201880065923.1. (7 Pages).
English Summary Dated May 18, 2023 of Notification of Office Action Dated May 7, 2023 From the State Intellectual Property Office of the People's Republic of China Re. Application No. 201880065923.1. (3 pages).
English Summary Dated Sep. 26, 2022 of Office Action Dated Sep. 13, 2022 From the State Intellectual Property Office of the People's Republic of China Re. Application No. 201880065923.1. (2 Pages).
Notification of Office Action and Search Report Dated Sep. 13, 2022 From the State Intellectual Property Office of the People's Republic of China Re. Application No. 201880065923.1. (9 Pages).

\* cited by examiner

ROBOTIC SYSTEM FOR MINIMALLY INVASIVE SURGERY

RELATED APPLICATIONS

This application is a National Phase of PCT Patent Application No. PCT/IL2018/051016 having International filing date of Sep. 6, 2018, which claims the benefit of priority under 35 USC § 119 (e) of U.S. Provisional Patent Application No. 62/554,658 filed on Sep. 6, 2017. The contents of the above applications are all incorporated by reference as if fully set forth herein in their entirety.

FIELD AND BACKGROUND OF THE INVENTION

The invention relates to the field of systems and methods for performing robotically controlled, minimally invasive, surgical procedures, especially for removal of tumors, and especially for brain tumors, and including the preliminary investigation of the nature of the region on which the procedure is to be performed.

In US published Patent Application No. US 2014/0025088, having common inventors with the present application, there is described a robotic device for performing minimally invasive neurosurgical procedures, using a cannulated needle for insertion into the cranial tissue, with a flexible inner needle disposed coaxially within the cannulated needle, and able to exit the cannulated needle at angles up to 90° to the axis of the cannulated needle, such that access is obtained to tissue located laterally to the exit aperture of the device. Rotation of the cannulated needle enables access to tissue disposed at any angle azimuthal to the cannulated needle axis. The flexible inner needle is advantageously of the self-reassembling structure, of which several alternative embodiments are described in the above referenced application.

A preoperative treatment plan, based on any preoperative imaging modality, such as MRI or CT, is used in order to determine the three-dimensional location and extent of any tissue anomaly, such as a tumorous growth, within the patient's brain tissue. These preoperative images may then be used to determine the surgical procedure to be performed on the growth. Motion of the cannulated needle and the flexible inner needle are robotically controlled, with the robotic coordinate system registered to the patient's skull and hence to the details on the preoperative images. However, the existence of brain shift effects, due to leakage of cerebrospinal fluid (CSF), treatment on the brain matter and the insertion of the robotic probe into the brain tissue, makes such a system in which the treatment location is based solely on the expected position of the previously imaged targeted tissue, a risky or even dangerous procedure, since it is not known where the treatment is actually being performed. There therefore exists a need for a robotically controlled surgical system, which takes into account motion of the tissue being operated on, which overcomes at least some of the disadvantages of prior art systems and methods, and enables the treatment to be performed safely only on the diseased tissue which it is desired to treat while leaving any healthy tissue intact.

The disclosures of each of the publications mentioned in this section and in other sections of the specification, are hereby incorporated by reference, each in its entirety.

SUMMARY OF THE INVENTION

The present disclosure describes new exemplary systems and methods for performing minimally invasive surgical procedures, especially for removal of tumors, and especially for brain tumors. In order to avoid the destruction of healthy tissue, the system uses a robotically inserted therapeutic probe, which first detects the presence of tumorous tissue as it proceeds on a pre-planned path through the patient's tissue, before performing any irreversible therapeutic procedure on the tissue, such as ablation. This pre-treatment detection procedure is thereby essentially able to avoid the destruction of healthy tissue. Additionally, even if no diseased tissue is self-detected by the probe, but preoperative images indicate the likelihood of tumorous tissue in a certain region, the probe can be used to confirm the presence of tumorous tissue at that expected location, before the actuation of any ablative procedures. The need for such concomitant intraoperative real-time detection procedures with the therapeutic treatment is necessary in order to ensure that the therapeutic process indicated in a preoperative surgical plan is only performed on tumorous tissue, and that reliance is not made solely on the supposed position of the tumorous tissue as indicated by preoperative images. This is particularly important for neurosurgical operations performed on the brain, since for such applications, reliance on preoperative images may not be accurate due to brain shift occurring during the procedure. Damage to healthy tissue is thus largely avoided. This real-time detection and treatment of the tumor is thus highly advantageous in such neuro-surgical procedures. The apparatus and procedures can be used to remove both benign or malignant growths.

In order to illustrate the apparatus and its methods of use, the example of brain surgery is used in this disclosure, this being an application where it is particularly advantageous to use the currently described system and method. The system uses a combination detection and therapy probe as the inner needle or probe of the type of device described in the above referenced US 2014/0025088. This probe exits from the outer cannula through an orifice, preferably disposed at right angles to the longitudinal axis of the outer cannula. The inner needle may have a self-reassembling structure, such that it can change its assembly state while negotiating the sharp curve of the exit orifice within the confines of the outer diameter of the outer cannula, and reassemble itself into a rigid needle or probe after exiting the orifice. Thus, the term "flexible" used in the above referenced US 2014/0025088 when relating to the inner needle or probe, and as used in this disclosure, and as claimed herein, is understood to include such a reassembleable needle or probe. Such a combination detection-and-therapy needle or probe can be manipulated in incremental steps within the brain tissue, to ensure confirmation of abnormal tissue detection before any treatment of any incremental volume of the brain. By this means, therapy is performed only on tumorous tissue, while healthy tissue is essentially protected from damage. Thus both the detection and the therapy are performed on a very local volume, with robotic control of the insertion and rotation of the outer cannula, and of the extent of protrusion of the flexible inner probe, ensuring that the brain tissue is examined and treated in all three dimensions, with minimal damage to surrounding healthy brain tissue. The resolution of the probe motion can be such that volumes of less than 1 ml. can be effectively treated, without substantial damage to surrounding healthy tissue.

The tumor detection tool, located at the distal end of the flexible or self-reassembling inner probe, can utilize any of a number of alternative tumor detection methods, such as the use of 5-aminolevulinic acid (5-ALA) induced fluorescence detection, an ultrasound detector, direct optical detectors (other than the 5-ALA method mentioned above), electrical impedance measurements, or any similar detection procedure for tumorous tissue. The therapeutic tool, also located at the distal end of the flexible or self-reassembling inner probe, may be any local ablation device, such as laser ablation, RF ablation, cryo-ablation, or the like.

In order to enable the detection and treatment elements of the probe to negotiate the sharp, preferably 90° bend at the cannula orifice, and to achieve this within a cannula preferably having an inner diameter of no more than 3 to 4 mm., the detection modality may advantageously be based on an optical procedure, which can be implemented in a thin fiber optical arrangement, with target illumination and returned spectral analysis signals being propagated through a single fiber or a graded core fiber, or with a fiber optical illumination delivery and a spectrally filtered photo-detector at the end of the probe. Electrical impedance measurements and ultrasound probing can also be achieved in such a flexible or self-reassembling inner probe arrangement, such as any of those described in the above referenced published patent application US 2014/0025088. Likewise, the ablation of any tumorous tissue detected may advantageously be performed by a higher powered laser ablation beam, transmitted down a fiber. Alternatively, electrical or ultrasound ablating modalities can also be provided within very tight radial dimensions. A working channel, typically provided down the inner flexible or self-reassembling probe needle, can be used for providing irrigation fluid, or for aspirating the condensed fluid to increase the cutting rate. Whatever methods are used, the detector tool can be used in order to close the loop of the robotic system motion control, such that the detection and treatment process can be performed fully automatically.

The total robotic surgical procedure may include the following steps:
(i) imaging, such as by MRI or other imaging modes capable of providing the contrast and resolution required, and delineation of the tumor on the images through a computer console or a monitor;
(ii) mounting the robotic system on the patient's skull, m a position identifiable to the preoperative images;
(iii) registration of the image data to the robotic system;
(iv) drilling a keyhole within the skull; and
(v) automatic incremental robotic steps of detection-therapy-motion, based on the preoperative imaging data.

First, imaging of the patient with markers attached to the skull is performed. These images are registered to the robotic coordinate system after attaching the robotic system to a stereotactic frame whose position is determined in the preoperative images by identification of the position of the markers. Alternatively, the robotic system can be attached directly to the skull. The robotic procedure does not rely only on this registration, because the occurrence of brain shift before or during the procedure, may make this method inaccurate. Instead, the system uses the preoperative images to obtain an expected region of interest, but then combines real-time tumor detection for maximal safety, as will be explained further below. The physician then marks the tumor margins on the three-dimensional image set. This marked volume defines the three-dimensional limits for the robotic motion range during the procedure. Next, the physician drills a small keyhole in the skull for external cannula needle entry along the safest path to the tumor as has been determined by the preoperative images. In this respect, the preoperative imaging is performed in order to provide the approximate position of the tumor, on the basis of which, the physician knows where to drill the keyhole entry aperture, and in which direction the robotic control needs to align the device for its insertion, while the actual treatment is done using local correction with the detection probe on the end of the inner needle probe. The robotic controller should preferably be configured such that the outer cannula needle is inserted no further than the proximal edge of the tumor, so that the treatment can begin with the most proximal edge of the tumor. Once the outer cannula has reached the proximal area of the tumor, the robotic controller then moves the flexible or self-reassembling inner needle out of the lateral orifice of the outer cannula, preferably at an angle of 90° to the axis of the outer cannula, and into the brain tumor. From this moment on, the procedure is performed automatically according to the following workflow:

(i) the detection tool is activated;
(ii) if the tissue is found to be cancerous, local treatment is performed followed by suction of the treated tissue (optional);
(iii) the inner needle then makes one step of motion (typically approximately 1 mm laterally), and the detection tool is again activated;
(iv) if the tissue is found to be diseased, therapy is again performed to remove that volume of cancerous tissue, followed by another step of lateral motion out of the aperture;
(v) if, on the other hand, any new region of tissue is found to be healthy, it is assumed that the outer lateral extent of the tumorous tissue has been reached, and the inner needle is fully withdrawn. In situations where the tumorous tissue is such that there is a region of healthy tissue before meeting another node of tumorous tissue, the surgeon relies on the preoperative images to decide how to proceed—whether to push the inner probe through the healthy tissue without performing any tissue ablation, or whether to treat the tumorous tissue by access from another trajectory;
(vi) an outer cannula needle rotation of an incremental angle, such as 1 degree, is performed, and the combination detection-therapy steps (i) to (v), are repeated at the new azimuthal angle;
(vii) this procedure is repeated until the needle has completed up to 360 degrees of rotation, detecting and ablating all of the tumor at that lateral level, up to the outer margin limits of the tumor marked on the display;
(viii) the inner needle is fully withdrawn from the tissue, such that it is stowed within the outer cannula needle, which is then moved downward an incremental distance, such as 1 mm., and the entire procedure is repeated at the new distal level, and so on, until the entire tumor volume is treated.

The pre-operative images are used by the system to indicate the approximate starting point for the real-time detection procedure. However, the shape of the cancerous region may be irregular, having, for example, additional cancerous tissue that is laterally remote from the main tumorous region, but with a region of healthy tissue in between. According to the described motion system above, a system based only on real time detection may misinterpret the internal needle's reaching healthy tissue as the end of the extent of the tumor, and would cease its incremental lateral motion and begin rotational motion, thus failing to reach the additional lobe of cancerous tissue. Therefore, the control system should incorporate an interactive procedure, by which the data from the preoperative images may be used in order to override the motion decisions determined by the real time detection tip when necessary, in order to ensure that all delineated regions of the tumor are reached. Such an algorithm could determine an order in which the tissue is treated that is efficient and logical and takes into account the order of the three types of movement: lateral movement, then rotation, then downward—in a way that ensures that all the unhealthy tissue is treated.

For the external cannula needle rotation and downward motion, the inner needle mechanism is fully withdrawn inside the external cannula needle, to prevent unnecessary damage to the brain tissue. The physician monitors the robotic needle motion on preoperative images and the real-time detection tool results, and may stop the procedure at any time should the brain shift be at such level that location of the treatment relative to the intended location is unclear.

According to a further implementation of the systems and methods of the present disclosure, a real-time tumor detection and therapeutic tool is described, which can be used independently of the robotic insertion device described hereinabove. Existing therapeutic tools for neurosurgery, including Cavitron ultrasonic surgical aspirator (CUSA), RF, cryo-thermal treatment, and others, are intended for tumor ablation based on either or both of preoperative imaging such as MRI and CT, and intraoperative navigation systems that allow ultrasound imaging in between the therapy episodes. The present application discloses a real-time tumor detection tool that is incorporated in the tip of a therapeutic tool and alerts the surgeon in real-time when a healthy tissue is reached, such that the treatment is prevented from being performed on that tissue, and at the same time maximizes the cancerous tissue excision/ablation.

Although the system has been described in this disclosure in an exemplary application for the removal of cranial tumors, it is to be understood that this is only one example of its use, and is not intended to limit the claimed inventions, and that the system can be used for removal of cancerous growths in any part of the subject' anatomy, provided that adequate anchorage can be provided for mounting the robotic device thereupon. The apparatus can be so anchored either directly into bone parts, or by use of straps to attach the apparatus to other body parts.

There is thus provided in accordance with an exemplary implementation of the devices described in this disclosure, a system for detection and treatment of diseased regions in a tissue of a subject, comprising:
  (i) a rigid cannula needle having a laterally directed distal orifice and a flexible inner probe capable of deployment laterally from the rigid cannula needle through the orifice, the flexible inner probe having at its distal end a tip comprising:
    (a) a sensor element configured to detect the state of the tissue in the region of the tip, and
    (b) a treatment element in proximity to the sensor element, configured to treat regions of the tissue detected by the sensor element as being diseased,
  (ii) a robotic mechanism for moving the probe into a selected region of the subject's tissue where preoperative images indicate the presence of a diseased region of tissue, and
  (iii) a controller adapted to provide commands to the robotic mechanism to move the rigid cannula needle and the flexible inner probe incrementally and co-operatively within the selected region of the subject's tissue, such that essentially all diseased regions of tissue within the volume of the subject's tissue are treated.

In any of the above-described systems, the tissue may be a brain tissue of the subject. Furthermore, in such systems the sensor element may be a fiber optical fluorescence probe, and the treatment element may then be the tip of a fiber delivering an ablative laser beam. Such a fluorescence probe may be adapted to detect the presence of fluorescence arising from UV excitation of 5-aminolevulinic acid (5-ALA).

Additionally, in any of these systems, the sensor element may be any of an ultrasound imaging probe, a direct optical detection probe, or an electrical impedance measurement probe, and the treatment element may be either of a set of radio frequency ablation electrodes or a cryo-ablation tip.

Regarding the above described system, the flexible inner probe may comprise self-reassembling elements. Furthermore, the orifice may be directed essentially at right angles to the axis of the rigid cannula needle.

Finally, such systems may further comprise a set of markers adapted to be mounted on the body of the subject for rendered in a preoperative image set, and the robotic mechanism may be adapted to be mounted on the body of the subject in a known position relative to the markers, such that the robotic mechanism may be registered to the preoperative image set.

Yet other implementations described in this disclosure, perform a method of detection and treatment of diseased regions in the tissue of a subject, comprising:
  (i) determining the three dimensional extent of the diseased regions of tissue,
  (ii) inserting into the tissue, a rigid cannula needle having a laterally directed orifice and a flexible inner probe capable of deployment laterally from the rigid cannula needle through the orifice, the flexible inner probe having at its distal end, a tip having detection and treatment elements,
  (iii) deploying the flexible inner probe from the laterally directed orifice in incremental steps, and determining at each step, by means of the detection element, whether tissue in the region of the tip is diseased,
  (iv) if the tissue in the region of the tip is diseased, actuating the treatment,
  (v) continually repeating the deploying of the flexible inner probe after performing successive incremental deployment steps of the rigid outer cannula in longitudinal and rotational directions, and
  (vi) repeating steps (iii) till (v) until the detection element in the tip has been deployed through the whole of the three dimensional extent of the diseased regions of tissue, such that the whole of the diseased regions of tissue have been treated.

In such a method, the tissue may be the brain tissue of the subject. Furthermore, in any of such methods, the detection element may be a fiber optical fluorescence probe, and the treatment element the tip of a fiber delivering an ablative laser beam. In such cases, the detection element may alternatively an ultrasound imaging probe, and the treatment element may be either a set of radio frequency ablation electrodes or a cryo-ablation tip. Finally, in any of these described methods, the flexible inner probe may comprise self-reassembling elements, and the orifice may be directed at right angles to the axis of the rigid cannula needle.

There is also provided a further method of surgical treatment of a subject, comprising:
  (i) delineation of a region to be treated of the subject's tissue on a preoperative image set,
  (ii) mounting on the subject's body in proximity to the region, a robotic system comprising a cannula needle having a laterally directed orifice at its distal end, (iii) inserting the cannula needle into the subject's tissue until the orifice reaches a selected lateral level of the region to be treated,
(iv) inserting into the cannula needle, a flexible probe such that its distal end exits the laterally directed orifice, the flexible probe having a tip at its distal end comprising detection and treatment elements,
(v) using the detection element to determine whether the portion of the tissue adjacent to the tip requires treatment, and if so, actuating the treatment element,
(vi) advancing the tip incrementally, and repeating step (v) until the tip reaches tissue which does not require treatment,
(vii) withdrawing the flexible probe into the cannula needle, rotating the cannula needle incrementally, and repeating step (v) and (vi);
(viii) repeating step (vii) until all of the lateral level has been covered,
(ix) withdrawing the flexible probe into the cannula needle, and further inserting the cannula to another lateral level, and
(x) repeating step (v) to (ix) until all portions of the subject's tissue requiring treatment have been treated.

In such a method, the selected lateral level may be the proximal edge of the region to be treated, or the most distal edge of the region to be treated, or any other suitable level.

Finally, such a method may be applied on tissue which is a brain tissue of the subject, and the robotic system may then be mounted rigidly on the subject's skull. In such an implementation, using the detection element to determine whether the portion of the brain tissue proximal to the tip requires treatment may enable the provision of compensation for the effects of brain shift.

BRIEF DESCRIPTION OF THE SEVERAL VIEWS OF THE DRAWINGS

The present invention will be understood and appreciated more fully from the following detailed description, taken in conjunction with the drawings in which.

DESCRIPTION OF SPECIFIC EMBODIMENTS OF THE INVENTION

Figure 1:
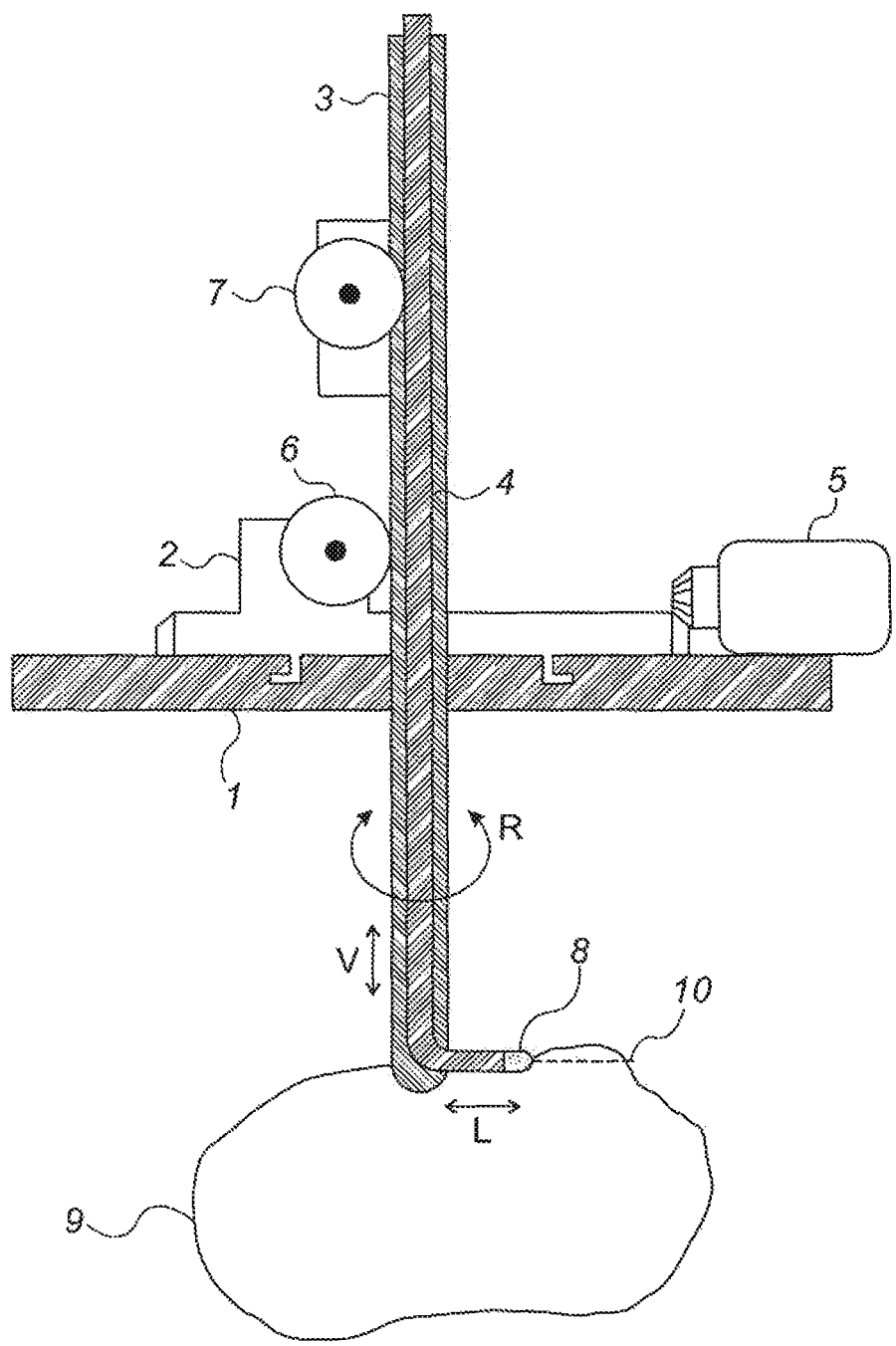
FIG. 1 illustrates schematically an exemplary implementation of an exemplary robotically controlled neurosurgical apparatus, according to the present disclosure.

Reference is now made to FIG. 1, which illustrates schematically an exemplary implementation of a robotically controlled neurosurgical apparatus according to the novel designs presented in this disclosure. In a novel arrangement, the inner flexible needle probe 4 has a combination detection and treatment module 8, at its distal end. Further constructional and operational details of various implementations of this detection and treatment module are shown hereinbelow. The other features are the external cannula needle 3, and the various components for providing the affixation of the apparatus on the subject's skull, and the robotically controlled mechanical motion of the probe 4. The latter includes a base section 2, which is rotatably mounted on a main base 1, which should be affixed to the subject's skull. Rotation of the base section 2 around the main base 1 may be performed by means of a robotic actuation motor 5, which should also include an angular position encoder, so that the angular orientation of the base section 2 is known.

The insertion of the internal flexible needle probe 4 may be controlled by means of a robotic motor and encoder 7, or by means of a linear motor (not shown). Alternatively, the inner flexible needle probe 4 can be moved from its proximal end section protruding from the external cannula 3. The linear insertion and extraction motion of the complete double needle assembly relative to the base plate may be controlled by means of another motor and encoder 6. If the system is to be used with MRI intraoperative imaging, linear or rotary piezoelectric motors may advantageously be used to provide the motion.

The apparatus of FIG. 1 is used by coordinated robotic motions of the three independent axes, the first marked V (for vertical, though not intended to be limited to a spatially or gravitationally vertical direction), activated by motor 6 to drive the depth of penetration of the external cannula needle 3: the second marked L (for lateral) activated by motor 7, to drive the amount of the lateral extension of the internal flexible needle probe 4 from the orifice of the external cannula needle 3: and the third marked R (for rotational), activated by motor 5, to rotate the complete combined needle assembly by rotating base section 2.

Figure 4:
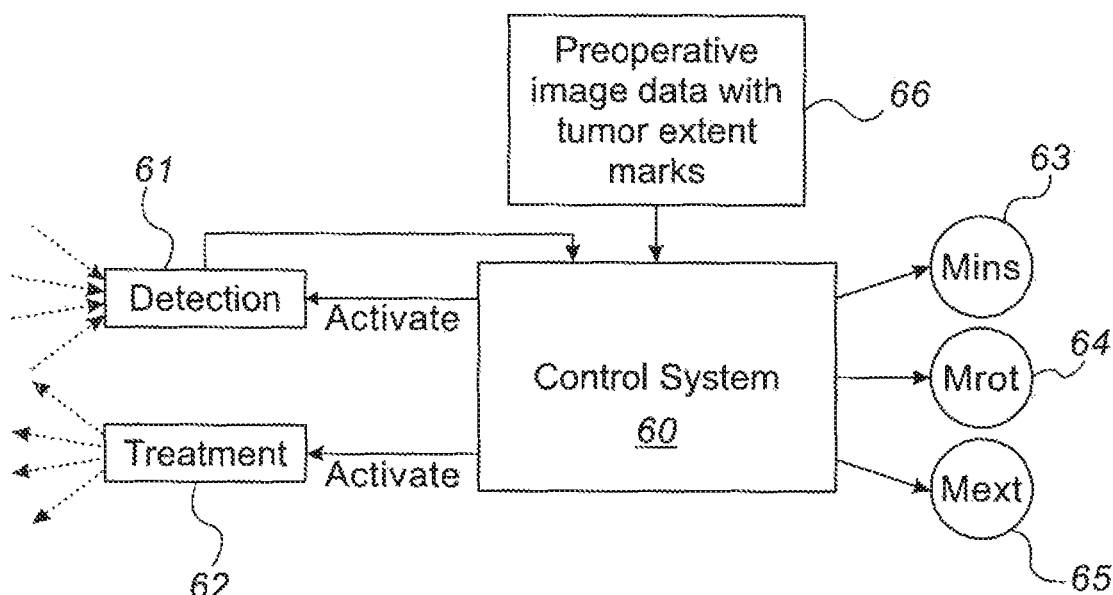
FIG. 4 is a schematic block diagram showing the control system and controlled elements of the apparatus of FIG. 1, for executing the method of FIG. 3.
Figure 5:
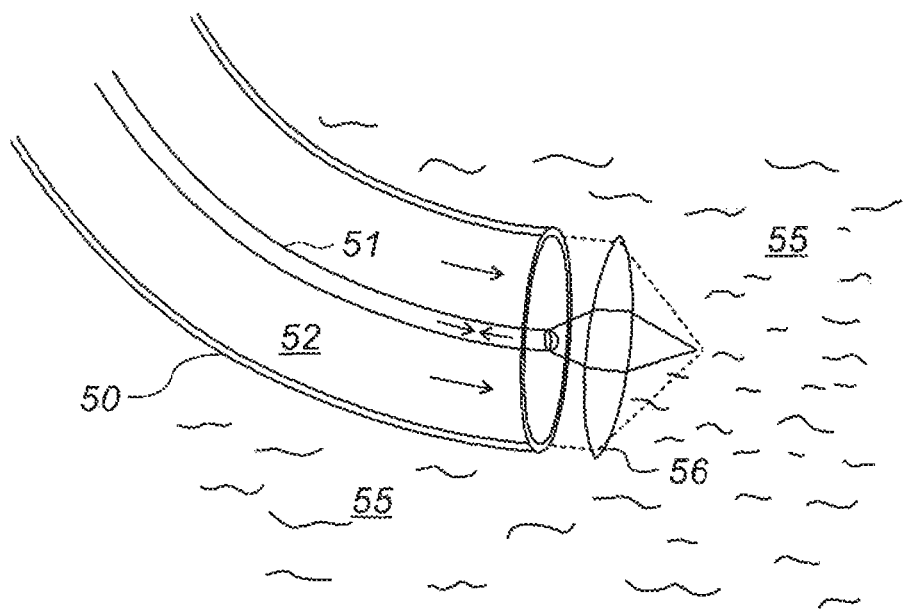
FIG. 5 illustrates schematically a first fiber optical in which both the detection and the ablation treatment of the tissue is performed optically.
Figure 6:
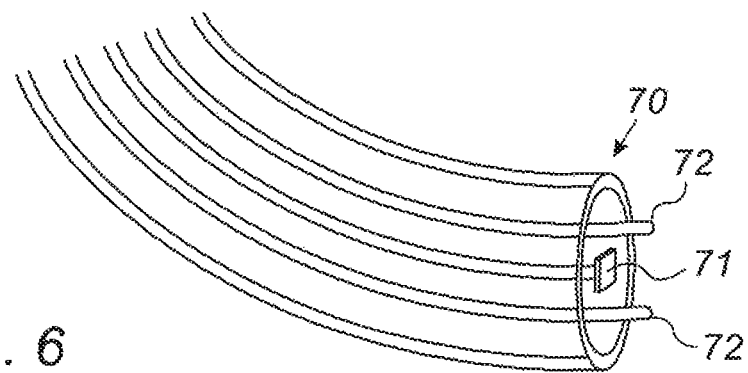
FIG. 6 illustrates schematically an alternative structure for the combination detection/treatment tip, using an ultrasound probe for determining the nature of the tissue encountered, and an electro-ablation head for destroying the tumorous tissue.

The distal end of the flexible needle probe 4 comprises a tip region 8, into which there is integrated a detection module, which is able to analyze the tissue within the region of sensitivity in front of the tip, and to determine whether the tissue is of a tumorous nature or is healthy tissue. FIGS. 4 to 6 hereinbelow describe a number of structures whereby this detection can be performed. Once the detection module has confirmed the presence of tumorous tissue immediately in front of the tip region 8, a signal is transferred back to the system control unit, not shown in the drawings but which is typically microprocessor or computer-based, which outputs another signal in order to actuate the treatment module. The treatment module ablates or otherwise destroys the either benign or malignant tissue within the effective range of the treatment module. Additionally, if a procedure such as the Fine Needle Aspiration Biopsy (FNAB) procedure is being performed as the surgical treatment, the present described apparatus and methods ensure accuracy in aspirating cells from the tumorous area. Independently of the particular method of cell destruction or extraction used, the composite detection/treatment probe described in the present disclosure, is able to autonomously detect and either destroy or aspirate tumorous tissue within access of the flexible needle probe.

There is now described a specific manner of using the system of the present disclosure, defining the three independent motions which provide access to any point in a three-dimensional region on either side of the longitudinal axis of the inserted device. One important feature of this method is that the internal flexible probe 4 is ejected from the external cannula needle 3 at an angle equal to or close to 90° to the longitudinal axis of the external cannula needle 3. The probe tip 8, thus travels in a lateral direction away from the orifice of the external cannula needle 3. This feature has an important advantage in that it provides maximum access to the volume of a tumor 9, with minimum damage to healthy tissue around the tumor. By inserting the device such that its distal end just reaches the uppermost edge of the tumor 9, and by using lateral extension, the detection/treatment probe tip 8 is able to destroy tumorous tissue at the upper limit of the tumor 9 without harming any healthy cells, either by passage through that healthy tissue or by collateral damage during destruction of the tumorous tissue. Such damage may be caused if the orifice were angled at less than a right angle to the external cannula axis. In the latter situation, the probe tip would have to cross healthy tissue in order to reach the diseased tissue at the top edge of the tumor.

In use, the surgeon drills an access burr hole and inserts the device with its axis aimed at the center of the tumor 9, until the orifice reaches the top edge of the tumor 9, as expected by the preoperative images of the subject's skull. A more accurate procedure, which would take into account any effects of brain shift, would be to advance the device until it reaches a predetermined point above the expected top edge of the tumorous tissue, and to begin the search procedure from that point. However, brain shift in a proximal direction is generally less likely, such that without this additional step, the procedure is presumed to have good efficiency. The inner flexible probe then exits the orifice with the tumor detection module in the tip 8 operating, such that any tumorous material detected can then immediately be removed by operating the ablation function in the tip 8. The tip is advanced laterally until it reaches the outer edge of the tumor 10, at which point the detection unit will instruct the device controller that no further tumorous tissue is apparent, ablation is ceased, and the tip is withdrawn by the internal flexible probe into the external cannula. The entire device can now be rotated by an incremental angle, typically 1°, and the procedure repeated with the detection/ablation module removing tumorous tissue from another azimuthal angle at the level at which the orifice is stationed. Once this radial path has been cleared of tumorous tissue, the procedure is repeated at yet another incremental angle, until the entire circumferential slice of the tumor at the first lateral level has been removed. The device is then moved incrementally downwards, typically by 1 mm., and the entire procedure repeated at this new radial lateral level. The procedure is repeated at successive radial lateral levels until a level is reached where no tumorous tissue is found through the entire 360° rotation at that level, signifying that the flexible probe has reached the most distal and of the tumor. The tumor should then have been completely eradicated.

The method by which complete lateral slices are sequentially cleared of tumorous material, as described in the above procedure, is only one method by which a three-dimensional tumor can be removed from the brain of a subject. It is equally possible to perform the three-dimensional treatment process by choosing one azimuthal angle in which to clean a vertical segment of the tumor from top to bottom, similar in shape to a slice of fruit, followed by rotation of the orifice incrementally to a different azimuthal angle, where a second segment of the tumor is removed from top to bottom, and so on until the complete three-dimensional rotational volume of the tumor has been treated. This method may be less advantageous than the first described method of clearing horizontal lateral slices one after another, since clearing a parallel shaped radial slice of tissue involves multiple traverses of the inner sections of the radial slice as the slice is rotated, leading to wasted procedure time. However, the methods of the present disclosure are not meant to be limited to any particular scanning algorithm to cover the entire volume of a tumor, though some motion combinations may be more treatment-time efficient than others.

Figure 2:
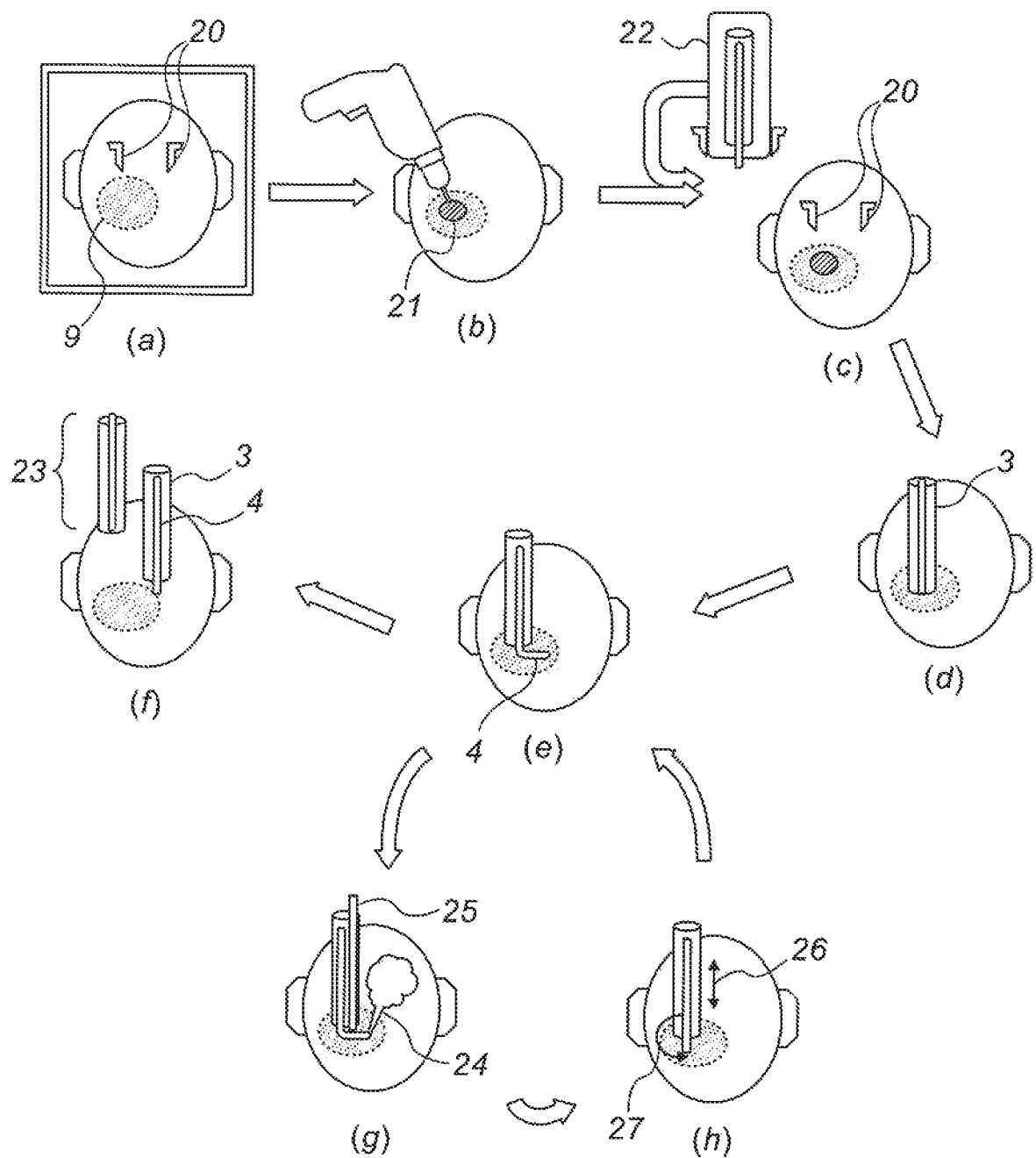
FIG. 2 is a pictorial flow chart representation of a typical method by which the steps mentioned below are executed using the apparatus of FIG. 1.

Reference is now made to FIG. 2 which is a pictorial flow chart representation of a typical manner in which the steps described above are executed using the apparatus of FIG. 1.

In step (a), preoperative MRI images are taken of the subject's skull, with markers 20 to define spatial reference positions on the skull, and the extent of a tumor 9 revealed in the image is delineated on the images.

In step (b), the surgeon drills a keyhole 21 in the skull, appropriately positioned to provide safest access to the tumor.

In step (c), the robotic device 22 is attached to the skull in a position which has a known relationship to the markers 20 shown in the preoperative images, and registration is performed of the robotic coordinate system relative to the tumor 10, as shown in the preoperative images.

In step (d), the external needle 3 of the device is inserted into the brain until it reaches the tumor layer closest to the insertion point on the skull, as expected from the preoperative cranial images and the delineated position of the tumor. This insertion procedure, starting at the most proximal position of the tumor, may be the simplest method of covering the entire volume to be treated, but it is to be understood that the treatment trajectory and envelope may also be commenced within the suspected tumorous volume, or at its distal end and working back up proximally.

In step (e), the inner detection probe 4 is passed through the exit orifice in the external needle, and into the brain tissue, and the real-time detection sensor is activated to determine whether or not the tissue at the point to which the tip has reached is tumorous or not.

If the tissue is shown to be healthy, then in step (f) the inner needle 4 is withdrawn into the outer needle 3, followed by withdrawal 23 of the entire device.

If on the other hand, the tissue is shown to be tumorous, then in step (g), therapeutic ablation of the tissue is performed, shown in this figure (FIG. 2) as being laser ablation 24, with suction 25 applied to remove the ablation by-products.

In step (h), the inner needle, after completion of the ablation treatment in step (g), is moved an incremental step outwards 26, or alternatively the assembly rotates 27 or moves downward, all depending on the location reached.

After reaching its new position, as indicated by the step (i), the real-time detection probe is again activated, as in step (e), to ascertain whether the tissue at the new point to which the tip has reached, is tumorous or not.

The automatic recursive robotic steps of detection-therapy-motion, through steps (e), (g) and (h) are then performed until the entire tumor has been removed.

Figure 3:
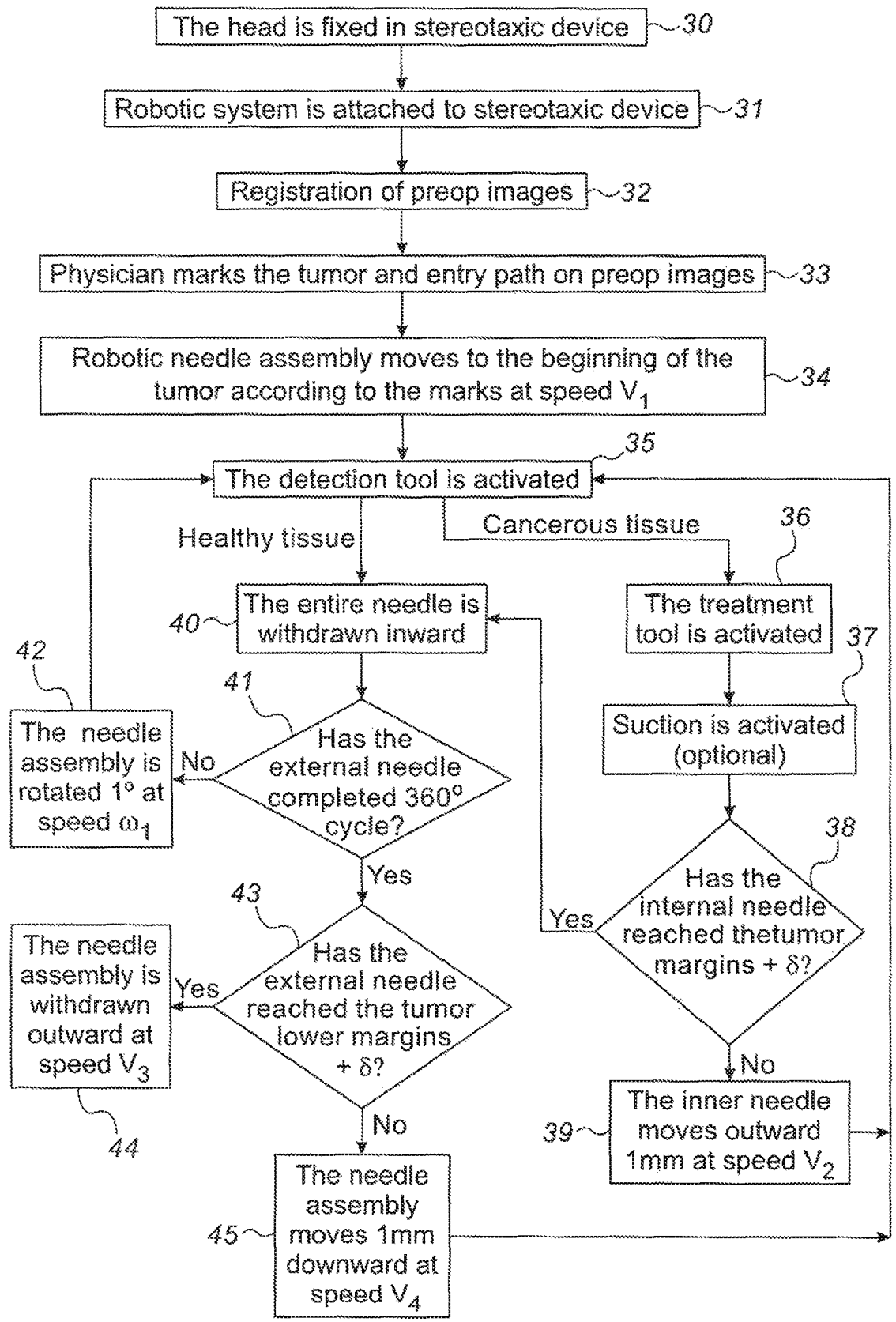
FIG. 3 is a flowchart of one exemplary method of the steps performed in the insertion of the detection/therapy probe tip into the patient's brain.

Reference is now made to FIG. 3, which is a flowchart of one exemplary method of the steps performed in the insertion of the detection/therapy probe tip into the patient's brain, such that the detection/therapy probe covers the whole of the volume of a suspected tumor.

In step 30, a stereotactic frame or the device base 1 is affixed to the subject's head, and preoperative images are generated of the patient's head, with markers or screws indicating the position of the frame or base.

In step 31, the robotic device itself is affixed to the frame or to the base.

In step 32, the robotic device coordinate system can be registered to the coordinate system of the subject's imaged head, by means of the markers or screws associated with the stereotactic frame or the base, which appear in the preoperative images of the head.

In step 33, the physician marks on the preoperative images, the extent of the tumor and the selected entry path that will lead directly to the tumor region, and drills a burr hole in the skull to enable access to the selected entry path.

In step 34, the robotic control system moves the complete needle assembly down the selected path to a position such that the flexible needle probe orifice is opposite the upper boundary of the tumor, as determined by the physician's marks on the preoperative images. As previously explained in connection with step (d) of the pictorial flow chart of FIG. 2, this insertion procedure, starting detection and treatment at the most proximal position of the tumor, may be the simplest method of covering the entire volume to be treated, but it is to be understood that the treatment trajectory and envelope may also be commenced at a different preferred level within the suspected tumorous volume, or even at its distal end, with the probe working back proximally.

In step 35 the detection tool at the tip of the flexible needle probe is activated in order to determine the nature of the tissue in front of the probe. If healthy tissue is encountered, then in step 40, the flexible needle probe withdrawn inwards until it is no longer protrudes from the device, and the complete needle assembly can then be rotated by a predetermined incremental angle without damaging the surrounding tissue, to continue searching for cancerous tissue around the position of the lower end of the complete needle assembly.

On the other hand, if in step 35, cancerous tissue is encountered, then in step 36, the therapeutic treatment tool in the tip is activated in order to ablate or otherwise destroy the cancerous tissue.

In step 37, suction is optionally activated in order to remove the ablated material.

In step 38, the control system determines whether the tool has reached the outer margin of the tumor, as determined by the physician's marks on the images, or, in order to take into account any brain shift, as determined by the physician's marks in addition to at least one additional incremental step in order to generate a positive determination of the extent of the tumor by real time sensing, rather than an assumed extent using a preoperative image set.

If the outer margin of the tumor has not been reached, then in step 39, the flexible needle probe is moved downwards by a predetermined increment, typically 1 mm, such that the detection/treatment tool is moved outwards through the tumor by that predetermined amount. The path of the detection/treatment tool is indicated in the example shown in FIG. 1 by the dashed line in front of the tool. After the intended movement, the method returns to step 35 when the detection tool is again activated to determine the nature of the tissue where the probe tip is now located.

On the other hand, if in step 38, the outer margin of the tumor has been reached, as shown by the point marked 10 in FIG. 1 (possibly also including extra incremental motion to eliminate any effects of brain shift, and possibly also including ablation of a small additional increment of healthy tissue to ensure complete removal of the diseased tissue), the method returns to step 40, the entire assembly is rotated by the above-mentioned predetermined incremental angle, and the whole process of detection and treatment, as described in steps 35 to 39, is repeated at that new azimuthal angle.

In step 41, the control system checks whether the procedure has been performed at the present insertion level, over the entire 360° of rotation of the assembly. If not, then in step 42, the complete needle assembly is rotated by a further angular increment, and the whole process of detection and treatment, as described in steps 35 to 41, is repeated at that new azimuthal angle.

On the other hand, if the complete 360° rotation of the assembly has now been completed, then in step 43, the system control determines whether the external needle assembly has reached the lower margin of the tumor, as marked by the physician.

If step 43 indicates that the lower extent of the tumor has not yet been reached, then in step 45, the complete external needle assembly is moved downwards by a predetermined incremental amount, typically 1 mm, and the system returns the process to the procedure of step 35, where the detection tool is activated at the new insertion level of the complete assembly.

To ensure complete removal of the tumorous tissue, even when the lower margin of the tumor has been reached, it may be advisable to advance the complete assembly by one more incremental step, in order to sense whether any further cancerous tissue exists beyond the supposedly lower limits of the tumor. As an alternative, it is possible to incorporate a sensing element which faces in the direction of motion of the complete assembly, i.e. downwards in the drawings of this application, so that this possibility can be determined without the need to insert the assembly further than necessary.

If on the other hand, the system control determines that the external needle assembly has reached the lower margin of the tumor, as marked by the physician, and that no further diseased tissue is detected by the detection probe, including in an optional additional incremental insertion motion, then in step 44, the system withdraws the complete needle assembly, since the entire volume of the tumor is assumed to have been removed, and the procedure is terminated.

Reference is now made to FIG. 4, which illustrates schematically the control system of the presently disclosed device, including the sensing and controlled elements and their interaction. The control system itself may be a dedicated microprocessor or ASIC based controller or generic computer system, programmed to execute the method defined by the flow chart of FIG. 3, or a similar algorithm which can successfully perform the required actions to supervise the operation of the system.

At the outset of the procedure, the controller 60 inputs the data 66 obtained from the preoperative images generated of the region of interest of the subject (the brain in the embodiment used to describe the invention in this disclosure), including any markers entered onto the image set by the physician to delineate the expected outer boundaries of the tumorous tissue which is to be removed. The controller then actuates the external needle assembly insertion drive motor Ment 65, and advances the entire needle device until the orifice of the detection/treatment probe has reached the beginning of the tumorous tissue, as obtained from the data input 66.

In order to execute the insertion of the detection/treatment probe needle, an insertion drive motor Mins 63 is actuated by the controller 60, firstly generating a gross movement of the detection/treatment probe needle such that it emerges from the external needle assembly, and also generating predetermined incremental motions of the probe to advance it carefully through the tumorous region. At each increment of the insertion procedure, the controller 60 receives inputs from the detector element 61 of the detector/treatment probe. Based on that input, the controller algorithm performs one of two actions:

(i) if the detection input indicates a diseased volume in front of the probe, it generates a command to actuate the treatment element 62 of the detection/treatment probe for a predetermined time, that time having been precalibrated according to the tissue destruction method and the input power used, to ensure complete destruction of the tissue in a volume in front of the detector element 61; or (ii) if the detection input 61 indicates healthy tissue, it generates a command to the insertion drive motor $M_{ins}$ 63 to advance the flexible needle probe by the predetermined incremental distance, followed by a command to the detection element 61 of the detection/treatment probe, to analyze the nature of the tissue in front of the new position of the probe.

When the controller receives a signal that the maximum lateral extent of the tumorous tissue has been reached, in accordance with the exemplary insertion algorithm used in this disclosure to explain the operation of the control system, a change in the azimuthal angle of the device should be performed. The controller first commands the insertion drive motor Mins 63 to completely retract the flexible needle probe to within the external needle assembly, so that no damage is caused to healthy tissue by an inadvertently protruding probe tip, and once assured, the controller generates a signal to the rotation motor $M_{rot}$ 64, to rotate the whole device by the predetermined incremental angle, followed by the repeated execution of the routine for sensing and treating another angular direction at the lateral plane being treated.

Finally, when the algorithm indicates that a complete rotational plane has been sensed and treated, the insertion drive motor $M_{ins}$ 63 is operated to withdraw the flexible needle probe to within the external needle assembly, to ensure no projecting probe length, after which the controller activates the insertion drive motor $M_{ext}$ 65, and advances the entire needle device distally by a predetermined incremental amount, in order to perform the whole procedure again at a new lateral plane within the subject. The controller continues in this manner until the whole of the tumorous volume has been eliminated.

Reference is now made to FIGS. 5 to 6 which show a number of alternative structures for the combination detection/treatment tip 8 of the inner flexible or self-reassembling needle probe 4.

FIG. 5 illustrates schematically a first optical implementation in which both the detection and the ablation treatment of the tissue 55 is performed optically using an optical fiber. The implementation shown in FIG. 5 is an endoscopic type of application, using a double clad fiber 50, When used for 5-ALA-Induced Protoporphyrin IX (PPIX) fluorescence testing, the fiber core 51 is advantageously used for the ultraviolet illumination used for the detection mode of the probe, since the core, being single mode, provides the best optical resolution. The UV illumination, generally in the range of up to 440 nm, may be focused onto the tissue being examined by a lens 56, and the presence of cancerous tumor cells is revealed by the excitation of the characteristic PPIX fluorescence in the 620 to 640 nm red region of the spectrum. The backscattered blueish light from healthy tissue and any red fluorescence light from cancerous brain tissue can be focused back down the fiber core 51 to the detection monitor (not shown in the drawing), where an image of the illuminated area can be displayed, or where spectroscopic image processing can be used to automatically determine the nature of the illuminated tissue, and to instruct the tissue ablating optical system to commence ablation accordingly. This ablation can be implemented simply by transmitting a high power laser beam down the inner cladding 52 of the double clad fiber. The laser beam wavelength should preferably be in a region that does not interfere with the optical fluorescence and detection procedure, such as in the near infrared. Impinging beam density must be sufficiently high for the tissue to be successfully ablated. In the embodiment shown in FIG. 5, the ablating beam is illustrated passing through the focusing lens 56, such that it achieves a sufficiently high power density on the tissue. In this implementation, it is assumed that the local heating spreads sufficiently laterally to also destroy tissue not directly at the focus point. However, if a sufficiently high density beam can be transmitted down the fiber, then no focusing lens would be required for the ablating beam, which would destroy all the tissue opposite the fiber exit aperture. In such a case the focusing lens 56 can be sufficiently small that it focuses only the imaging probe beam. Since the energy of the ablating beam should ideally be absorbed by the brain tissue, little of the incident beam is reflected back to the fiber, such that it should not interfere unduly with the detection imaging process.

As an alternative to the double clad fiber shown in FIG. 5, it is possible to perform the function of optical detection, but using a fiber having a double core, where one core is used for exciting the fluorescence and the other core for imaging the tissues thus excited. In such an implementation, the ablating beam can be transmitted either through the inner cladding, or through an additional fiber passed through a working channel in the flexible probe.

Reference is now made to FIG. 6, which illustrates schematically an alternative structure for the combination detection/treatment tip 70, using a miniature ultrasound probe 71 for determining the nature of the tissue encountered by means of ultrasound imaging, followed by electro-ablation using a pair of electrodes 72 excited by an RF voltage between them to perform electro-ablation of any tissue encountered that requires removal.

Combination detection/treatment tip configurations may also be used, with detection being optical and ablation by RF erosion, or vice versa, using ultrasound detection and optical ablation, or any other suitable combination of detection and treatment tools.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. A system for detection and therapeutic ablation of a diseased region in brain tissue of a subject by clearance of a segment of the diseased region along a sequence of successive paths of an ablation tip, the paths being sequenced to incrementally scan the ablation tip throughout the segment, and the system comprising:

a rigid cannula needle having a laterally directed distal orifice and a flexible inner probe capable of deployment laterally from said rigid cannula needle through said orifice, said flexible inner probe having at its distal end the ablation tip, and the ablation tip comprising a sensor element configured to detect a state of said brain tissue in the region of said ablation tip as a diseased state or a healthy state;
a robotic device configured to move said probe within the brain tissue of the subject; and
a controller adapted to instruct the robotic device with commands to move the ablation tip along one or more of said successive paths while ablating, each sequence of said successive paths beginning with an initial path, and each path of said sequence, after the initial path, is incrementally adjusted relative to a respective sequentially preceding path of said sequence, wherein the commands of at least one of the sequences of successive paths comprising:
(i) commands which insert the ablation tip into the tissue along an initial path of said sequence leading from the orifice toward a target position,
(ii) commands generated in response to a sensed state of said tissue in the region of said target position, wherein when said sensor element detects said healthy-state then the commands move said rigid cannula needle and said flexible inner probe within said tissue to at least withdraw outward the flexible inner probe, extracting it along same said path, and
(iii) commands which re-insert the ablation tip into the tissue along said successive paths in the sequence, each said successive path being incrementally adjusted relative to a respective sequentially preceding path to target a new target position within the diseased region; and
wherein the ablation tip operates during movement along the sequences of paths to perform therapeutic ablation which clears diseased tissue from the segment, and the increments of adjustment between paths of each sequence of paths are sized to move the ablation tip to clear by ablation a portion of a volume including the segment, the segment extending between the initial path in which said sensor element detects said diseased state and a last path of the successive paths in which said sensor element detects said diseased state.

2. A system according to claim 1, wherein said sensor element comprises any one or more of the group consisting of an ultrasound imaging probe, a direct optical detection probe, and an electrical impedance measurement probe.

3. A system according to claim 1, wherein said flexible inner probe comprises self-reassembling elements.

4. A system according to claim 1, further comprising a set of markers adapted to be mounted on the body of said subject for rendering in a preoperative image set, and wherein said robotic device is adapted to be mounted on the body of said subject in a known position relative to said markers, such that the robotic device is registered to said preoperative image set.

5. A method of detection and therapeutic ablation of a diseased region in brain tissue of a subject by clearance of a segment of the diseased region along a sequence of successive paths of an ablation tip, the paths being sequenced to incrementally scan the ablation tip throughout the segment, and the method comprising:
(i) inserting into said brain tissue a rigid cannula needle having a laterally directed orifice and a flexible inner probe capable of deployment laterally from said rigid cannula needle through said orifice, said flexible inner probe having at its distal end the ablation tip, and the ablation tip comprising detection and ablation elements;
(ii) deploying said flexible inner probe from said laterally directed orifice in incremental steps along a first path, the incremental steps being performed according to physician-marked limits for a range of robotic motion, and under the instruction of a robotic controller;
(iii) between the incremental steps, receiving, at the robotic controller, sensing data from the detection element indicative of whether tissue in the region of said ablation tip is diseased;
(iv) actuating the ablation, the actuating comprising the robotic controller generating a command actuating ablation, and instructing the robotic device with the command, wherein the controller is configured to perform the generating contingent on the sensing data indicating that tissue in the region of said ablation tip is diseased;
(v) withdrawing the ablation tip in response to the sensing data indicating that tissue in the region of said ablation tip is healthy; and
(vi) repeating said deploying of said flexible inner probe after performing successive incremental deployment steps of said rigid cannula needle in longitudinal and rotational directions;
wherein the ablation tip operates during the incremental steps of the first path and the successive incremental deployment steps to perform therapeutic ablation to clear diseased tissue from the diseased region within the segment, the segment being smaller than the physician-marked limits in a direction extending radially from the laterally directed orifice, and said being smaller is due to the withdrawing the ablation tip in response to the sensing data indicating that tissue in the region of said ablation tip is healthy; and
wherein the sequence of successive paths are paths along which the successive incremental deployment steps occur, and are incrementally adjusted in response to a sensed state of said tissue in the region of said ablation tip in one or more of the longitudinal and rotational directions by a distance sized to move the ablation tip to clear the segment, the segment extending between the first path and a last path of the sequence of successive paths along which the successive incremental deployment steps occur.

6. A method according to claim 5, wherein said tissue comprises brain tissue of the subject.

7. A method according to claim 5, wherein said detection element comprises a fiber optical fluorescence probe, and said ablation element comprises a tip of a fiber delivering an ablative laser beam.

8. A method according to claim 5, wherein said detection element comprises an ultrasound imaging probe.

9. A method according to claim 5, wherein said ablation element comprises at least one of the group consisting of a set of radio frequency ablation electrodes and a cryoablation ablation tip.

10. A method according to claim 5, wherein said flexible inner probe comprises self-reassembling elements.

11. A method according to claim 5, wherein said orifice is directed at right angles to the axis of said rigid cannula needle.

12. A method of surgical treatment of a subject by therapeutic ablation of brain tissue of a subject, the method comprising:
(i) delineating a region to be treated of the subject's brain tissue on a preoperative image set;
(ii) mounting on the subject's body in proximity to said region a robotic system comprising a cannula needle having a laterally directed orifice at its distal end;

(iii) inserting said cannula needle into the subject's tissue until said orifice reaches a selected lateral level of said region to be treated;

(iv) inserting into said cannula needle a flexible probe such that its distal end exits said laterally directed orifice, said flexible probe having an ablation tip at its distal end comprising detection and treatment elements, and insertion of said flexible probe being under the instruction of a robotic controller controlling the robotic system to proceed along a path constrained to be within the delineated region;

(v) receiving, at the robotic controller, sensing data from the detection element indicative of whether a portion of said tissue adjacent to said ablation tip requires treatment, and actuating said treatment element, the actuating comprising the robotic controller generating a command actuating treatment, and instructing the robotic system with the command, wherein the controller is configured to perform the generating contingent on the sensing data indicating that tissue in the region of said ablation tip requires treatment;

(vi) advancing said ablation tip incrementally, operating the ablation tip to perform therapeutic ablation to clear diseased tissue from the region to be treated, and repeating step (v) until said ablation tip reaches tissue which, based on the sensing data, does not require treatment;

(vii) withdrawing said flexible probe into said cannula needle in response to the detection of tissue which does not require treatment, rotating said cannula needle incrementally, and repeating steps (v) and (vi), each also along a path constrained to be within the delineated region;

(viii) repeating step (vii) around said lateral level;

(ix) withdrawing said flexible probe into said cannula needle and moving said cannula to another lateral level; and (x) repeating steps (v) to (ix) to complete treating the region to be treated;

wherein the incremental rotations of the cannula needle are sized to adjust a path along which the ablation tip incrementally advances to clear a segment of the region to be treated sequentially and in the direction of rotating the cannula needle, the segment extending circumferentially from the path of the advancing of step (vi), to at least one path of the repeating of step (viii), the segment being smaller than the delineated region in a direction extending radially from the laterally directed orifice, and said being smaller is due to the withdrawing in response to the detection of tissue which does not require treatment.

13. A method according to claim 12, wherein said selected lateral level is either at a most proximal level of said region to be treated, or at a most distal level of said region to be treated.

14. A method according to claim 12, wherein said robotic system is mounted rigidly on said subject's skull.

15. A method according to claim 14, wherein use of said detection element to determine whether the portion of said brain tissue adjacent to said ablation tip requires treatment provides compensation for the effects of brain shift.

16. The system according to claim 1, comprising a treatment element in proximity to said sensor element configured to treat said tissue in the region of said ablation tip; and wherein the controller generates the commands to selectively move the treatment element to treat tissue in the diseased state within the tissue of the subject, contingent on detection of disease-state tissue by the sensor element.

17. The system according to claim 1, wherein the controller is also adapted to generate the commands based on where preoperative images of the tissue of the subject indicate the presence of the diseased region of tissue.

18. A system according to claim 1, wherein the commands move the needle and the inner probe in coordinated robotic motions.

19. A system according to claim 1, wherein the system is configured to repeatedly detect the state of said tissue while the rigid cannula needle and the flexible inner probe move incrementally, and the controller generates commands according to the repeated detection.

20. A system according to claim 1, wherein the controller is adapted to generate and provide commands to move the rigid cannula needle incrementally toward an outer margin of tissue in the diseased state until tissue in the healthy state is detected, and then withdraw the flexible inner probe.

21. A system according to claim 20, wherein the controller is adapted to generate and provide commands to perform the motion to the outer margin of tissue followed by withdrawal a plurality of times, with an incremental rotation of the needle between each performance.

22. A system according to claim 21, wherein the controller is adapted to generate and provide commands to perform the incremental rotations through at least 360° a plurality of times starting from different withdrawn positions of the flexible inner probe.

23. A system according to claim 16, wherein said sensor element is a fiber optical fluorescence probe, and said treatment element is the tip of a fiber delivering an ablative laser beam.

24. A system according to claim 16, wherein said treatment element comprises any one or more of the group consisting of a set of radio frequency ablation electrodes and a cryo-ablation tip.

25. A system according to claim 23, wherein said fluorescence probe is adapted to detect the presence of fluorescence arising from UV excitation of 5-aminolevulinic acid (5-ALA).

26. The system of claim 1, wherein incremental adjustment of said each path relative to said respective sequentially preceding path is executed automatically based on detection of said diseased state or said healthy state by said sensor element.

27. The system of claim 1, wherein in said initial path the flexible inner probe reaches a predetermined point above the expected top edge of the tumorous tissue.

28. The system of claim 1, wherein the initial path of the sequence of successive paths in which said sensor element detects said disease-state and a last path of the sequence of successive paths in which said sensor element detects said disease-state are constrained within a physician-provided volume of the diseased region, and wherein the segment cleared along said paths being smaller than the physician-provided volume in a direction extending radially from the distal orifice, and said being smaller is due to the commands which withdraw the flexible inner probe when the sensed state comprises healthy-state tissue detected by the sensor element.

* * * * *